United States Patent [19]

Schuyler et al.

[11] Patent Number: 4,897,185

[45] Date of Patent: Jan. 30, 1990

[54] CELL PROCESSING APPARATUS AND METHOD

[75] Inventors: Robert J. Schuyler, Boulder; Robert L. White, Kittredge, both of Colo.

[73] Assignee: Cobe Laboratories, Inc., Lakewood, Colo.

[21] Appl. No.: 254,392

[22] Filed: Oct. 6, 1988

[51] Int. Cl.$^4$ .................... B01D 13/00; B01D 33/00
[52] U.S. Cl. ................................ 210/90; 210/132; 210/254; 210/257.2; 210/258; 210/259; 210/297; 210/314; 210/360.1; 210/416.1; 210/433.1; 604/5; 494/36
[58] Field of Search ............. 210/90, 130, 132, 254, 210/257.2, 258, 259, 297, 307, 314, 321.6, 360.1, 361, 416.1, 433.1; 494/36; 604/4, 5, 6; 422/72, 101; 435/311

[56] References Cited

U.S. PATENT DOCUMENTS

| | | | |
|---|---|---|---|
| 4,322,275 | 3/1982 | Jain | 604/6 |
| 4,416,654 | 11/1983 | Schoendorfer et al. | 604/6 |
| 4,680,025 | 7/1987 | Kruger et al. | 604/4 |
| 4,681,677 | 7/1987 | Kuh et al. | 210/130 |

OTHER PUBLICATIONS

Muul, Linda M., et al., "Large Scale Production of Human Lymphokine Activated Killer Cells for use in Adoptive Immunotherapy", *Journal of Immunological Methods*, vol. 88, (1986), pp. 265–275.
Muul, Linda M., et al., "Development of an Automated Closed System for Generation of Human Lymphokine—Activated Killer (LAK) Cells for use in Adoptive Immunotherapy", *Journal of Immunological Methods*, vol. 101, (1987), pp. 171–181.
Gilmore, M. J. M. L., et al., "A Technique for the Concentration of Nucleated Bone Marrow Cells for in Vitro Manipulation or Cryopreservation Using the IBM 2991 Blood Cell Processor", vol. 45, *Vox Sang.* (1983), pp. 294–302.
Wooten, M. J. O'Connor, "Use and Analysis of Saline Washed Red Blood Cells", *Transfusion*, vol. 16, No. 5, (1976), pp. 464–468.
Cobe Hemofilter Operating Instructions, 415039-000 Rev. A.
Tutunjian, Robert S., "Ultrafiltration Processes in Biotechnology", *Annals N.Y. Academy of Sciences*, vol. 413, (1983), pp. 238–253.
Tamura, T. and Takano, T., "A New, Rapid Procedure for the Concentration of C—Type Viruses from Large Quantities of Culture Media: Ultrafiltration by Diaflo Membrane and Purification by Ficoll Gradient Centrifugation", *J. Gen. Virol.*, vol. 41, (1978), pp. 135–141.

*Primary Examiner*—W. Gary Jones

[57] ABSTRACT

Using a membrane separating device to remove cell-free fluid from a suspension of cells to preconcentrate cells in the suspension prior to processing in a centrifuge.

10 Claims, 1 Drawing Sheet

CELL PROCESSING APPARATUS AND METHOD

FIELD OF THE INVENTION

The invention relates to concentrating cells, e.g., cells that have been removed from a patient and have been cultured and are being prepared for return to the patient.

BACKGROUND OF THE INVENTION

It is known to remove cells, e.g., lymphocytes, from a patient's blood, grow them in culture medium, harvest the cultured cells, and separate the cells from the culture medium and metabolites before returning the cells to a patient, e.g., Muul, Linda, M., et al., "Large scale production of human lymphokine-activated killer cells for use in adoptive immunotherapy", *Journal of Immunological Methods*, Vol. 88 (1986), pp. 265–275; Muul, Linda, M., et al., "Development of an automated closed system for generation of human lymphokine-activated killer (LAK) cells for use in adoptive immunotheraphy", *Journal of Immunolooical Methods*, Vol. 101 (1987), pp. 171–181. A Cobe Laboratories, Inc. (IBM) 2991 centrifuge has been used in such procedures to separate cells from the culture medium and metabolites prior to returning the cells to a patient. The cells are subjected to plural centrifuge operations with application of a rinse solution between centrifuge operations after the cells have been concentrated. The use of the 2991 centrifuge to concentrate and wash other types of cells is described in Gilmore, M.J.M.L., et al., "A Technique for the Concentration of Nucleated Bone Marrow Cells for in vitro Manipulation or Cryopreservation Using the IBM 2991 Blood Cell Processor", Vol. 45, *Vox Sano.* (1983), pp. 294–302; Wooten, M.J. et al., "Use and Analysis of Saline Washed Red Blood Cells", Vol. 16, No. 5, *Transfusion* (1976) pp. 464–468.

SUMMARY OF THE INVENTION

In general our invention features passing cells in a suspension through a membrane separating device in which cell-free fluid passes through a membrane in order to preconcentrate the cells before concentrating them further in a centrifuge. This significantly shortens the time necessary to concentrate cells and reduces centrifugal exposure of the cells.

In preferred embodiments, pumps are used to pump the cell suspension into the membrane separating device and to remove cell-free fluid from the membrane separating device; the cell suspension may be filtered prior to passing into the membrane separating device; a prime solution bag, a cell suspension reservoir, and a pressure monitor are provided upstream of the membrane separating device; a centrifuge reservoir bag is provided between the membrane separating device outlet and the centrifuge; a waste line is connected to carry cell-free fluid to a waste pump; and a bypass line is connected between the waste line and the outlet of the membrane separating device.

Other features and advantages of the invention will be apparent from the following description of a preferred embodiment thereof and from the claims.

DESCRIPTION OF THE PREFERRED EMBODIMENT

Figure 1:
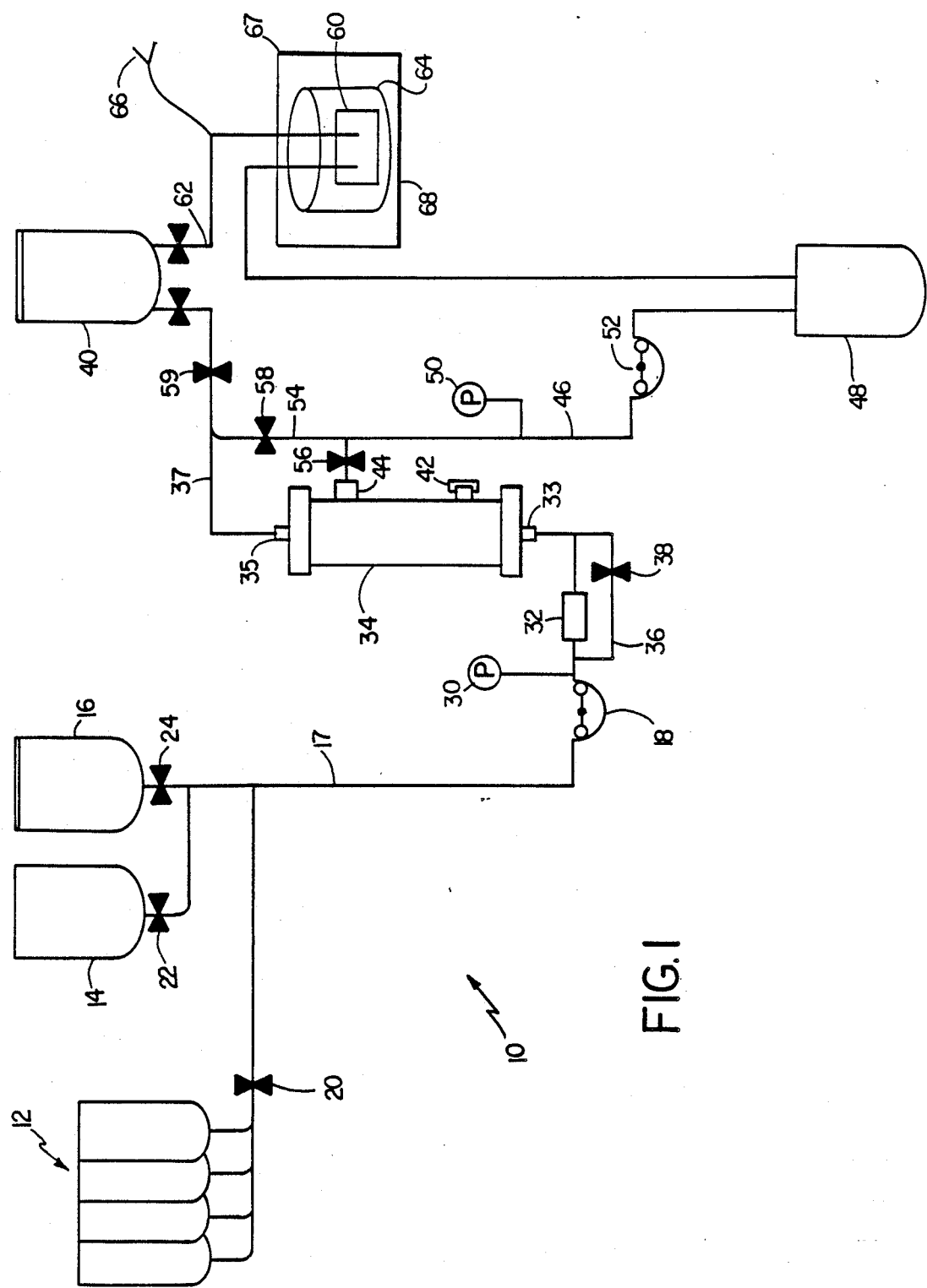

The preferred embodiment will now be described.

Drawing

The drawing is a hydraulic flow diagram of apparatus for processing a cell suspension according to the invention.

STRUCTURE

Referring to the figure, there is shown apparatus 10 for processing lymphocyte cells cultured in culture bags 12. Culture bags 12, prime saline bag 14 and rinse saline bag 16 are connected via line 17 to peristaltic cell suspension pump 18. Clamps 20, 22, and 24 control flow from culture bags 12, prime saline bag 14, and rinse saline bag 16, respectively. Pressure sensor 30 is connected to sense the pressure at the outlet of cell suspension pump 18.

Screen prefilter 32 is connected between the outlet of cell suspension pump 18 and inlet 33 of hollow fiber membrane separating device 34. Hollow fiber separating device 34 is available under the trade designation PAN 200 from Asahi, Japan; it includes polyacrylonitrile membrane hollow fibers having a molecular weight cutoff of 50,000 to 55,000. Membrane separating device 34 has high permeability to water and small molecules but very low permeability to proteins and particles of cellular dimensions. Inlet 33 and outlet 35 communicate through respective manifolds to the interiors of hollow fibers. Permeate ports 42, 44, communicate with the regions outside of the fibers within the outer shell of device 34. Bypass line 36 and clamp 38 thereon are connected in parallel with prefilter 32.

Outlet 35 of membrane separating device 34 is connected via line 37 to the inlet to centrifuge reservoir bag 40. Permeate port 42 is blocked, and permeate port 44 is connected via waste line 46 to waste bag 48. Pressure sensor 50 is connected to sense the pressure in line 46. Waste pump 52 is connected along line 46 to control pumping into waste bag 48. Bypass line 54 is connected between outlet 35 of membrane separating device 34 and waste line 46. Clamp 56 is used to control flow from permeate port 44, and clamp 58 is used to control flow through line 54. The outlet of centrifuge reservoir bag 40 is connected to centrifuge collection bag 60, located within rotating bowl 64 of centrifuge 67 (a 2991 centrifuge from Cobe Laboratories, Inc., not shown) via flow line 62. Wash line 66 is used to connect an alternate source of liquid to centrifuge collection bag 60, and supernatant line 68 is used to convey supernatant to waste bag 48.

OPERATION

In operation, lymphocyte cells that have been removed from a patient are cultured in bags 12, e.g., for three or four days. After culturing has been completed, apparatus 10 is used to process the cultured cells prior to returning them to the patient.

Clamp 22 is opened, and the solution in prime saline bag 14 is pumped through pump 18, filter 32, line 36, and the interiors of the hollow fibers in device 34 to prime the circuit and to rinse glycerol from separating device 34. Clamps 59 and 44 are closed so that the prime solution flows through lines 54, 46 to waste bag 48, tube 46 not being loaded into pump 52 at this time. During a portion of the prime, clamp 56 is open, and clamp 58 is closed, in order to prime the volume in separator 34 outside of the hollow fibers.

After the circuit has been primed, line 46 is loaded into pump 52, clamp 22 is closed, and clamp 20 is opened so that the cultured cells in suspension in bags 12 can be pumped through the circuit via pump 18. Clamp 58 is closed, and clamp 59 is opened. Prior to this time, the priming solution in the circuit flows through lines 54 and 46 into waste bag 48. After this time, the concentrated cell suspension from membrane separating device 34 flows into centrifuge reservoir bag 40 and from there into bag 60 in centrifuge 64.

Cell suspension pump 18 pumps the cell suspension into membrane separating device 34, and waste pump 52 pulls cell-free fluid across the hollow fiber membranes and pumps it into waste bag 48. The difference in pumping rates between cell suspension pump 18 and waste pump 52 equals the rate at which the concentrated cell suspension is delivered to centrifuge reservoir bag 40. For best efficiency, this rate is approximately the same rate as processing fluid in centrifuge 67. The processing in centrifuge bag 60 involves concentrating the cultured cells of interest and overflow of the supernatant through line 68. Filter 32 may be used to remove cellular clumps which could clog hollow fiber device 34. Bypass line 36 is used if filtration at filter 32 is not needed or if filter 32 becomes clogged. Pressure is monitored downstream of cell suspension pump 18 by pressure sensor 30 and on waste line 46 by pressure sensor 50.

After cell suspension bags 12 have been emptied, clamp 24 is opened and clamp 20 is closed to cause rinse saline to flow from bag 16 while pumps 18, 52 continue to pump to concentrate the cell suspension still in the circuit and transport it to centrifuge reservoir bag 60. The pumps continue to pump until sufficient rinse saline has passed through hollow fiber device 34. After the cells and rinse saline have been transported to centrifuge bag 60 and have been concentrated further therein, wash solution from wash line 66 is applied to remove media and metabolites from the cells collected in bag 60, according to the usual procedures. The cells are then resuspended and reinfused into the patient, also according to the usual procedures.

The pre-concentration step in separator 34 significantly shortens the time required for harvest and also reduces the centrifugal exposure of the harvested cells.

OTHER EMBODIMENTS

Other embodiments of the invention are within the scope of the claims. Other membrane separating devices can be used, for example, devices are available with larger maximum pore sizes up to 0.5 microns. Lymphocytes generally have diameters greater than 10 microns. These devices do not hold back proteins; the PAN 200 device described above does.

What is claimed is:

1. Apparatus for processing cells in a cell suspension comprising
    a membrane separating device connected to receive said cell suspension, said device including a membrane, said membrane being configured to pass cell-free fluid but not said cells through said membrane, said device having an outlet for a concentrated cell suspension, and
    means for receiving said concentrated cell suspension, said means including a centrifuge downstream of said separating device connected to receive said concentrated cell suspension from said outlet.

2. The apparatus of claim 1 further comprising pumps to control flow of said cell suspension through said separating device on one side of a membrane and flow of said cell-free fluid from the other side of said membrane so as to cause passage of said cell-free fluid therethrough.

3. The apparatus of claim 2 further comprising a pressure sensor upstream of said membrane separating device.

4. The apparatus of claim 2 further comprising a waste line connected to convey said cell-free fluid from said separating device, one said pump pumping liquid through said waste line.

5. The apparatus of claim 4 further comprising a bypass line between said waste line and a line connected to said outlet of said membrane separating device.

6. The apparatus of claim 1 further comprising a filter upstream of an inlet of said membrane separating device to filter said cell suspension prior to flowing into said membrane separating device.

7. The apparatus of claim 6 further comprising a bypass line around said filter and a clamp thereon to selectively block flow through said bypass line.

8. The apparatus of claim 1 further comprising a prime solution bag connected to the inlet of said membrane separating device.

9. The apparatus of claim 1 further comprising a cell suspension reservoir upstream of said membrane separating device.

10. The apparatus of claim 1 further comprising a centrifuge reservoir bag between the outlet of said membrane separating device and said centrifuge.

* * * * *